United States Patent [19]

Stipp et al.

[11] Patent Number: 5,142,072
[45] Date of Patent: Aug. 25, 1992

[54] SELECTIVE ESTERIFICATION OF LONG CHAIN FATTY ACID MONOGLYCERIDES WITH MEDIUM CHAIN FATTY ACID ANHYDRIDES

[75] Inventors: Gordon K. Stipp; Bernard W. Kluesener, both of Cincinnati, Ohio

[73] Assignee: The Procter & Gamble Company, Cincinnati, Ohio

[21] Appl. No.: 452,923

[22] Filed: Dec. 19, 1989

[51] Int. Cl.⁵ .............................................. C11C 3/08
[52] U.S. Cl. .................................................. 554/172
[58] Field of Search ........................... 260/410.7, 410.8

[56] References Cited

U.S. PATENT DOCUMENTS

| | | | |
|---|---|---|---|
| 1,959,590 | 5/1934 | Lorand | 260/410.7 |
| 2,236,516 | 4/1941 | Cahn | 260/410.7 |
| 2,411,567 | 11/1946 | Fisher | 260/410.7 |
| 2,520,139 | 8/1950 | Fuchs | 260/410.7 |
| 2,615,159 | 10/1952 | Jackson | 260/410.7 |
| 3,251,870 | 5/1966 | Dalby | 260/410.7 |
| 3,293,272 | 12/1966 | Freund | 260/410.7 |
| 3,410,881 | 11/1968 | Martin et al. | 260/410.7 |
| 3,551,464 | 12/1970 | Miller et al. | 260/410.7 |
| 3,595,888 | 7/1971 | Keiser et al. | 260/410.7 |
| 4,002,677 | 1/1977 | Naglierli et al. | 260/410.7 |
| 4,002,678 | 1/1977 | Naglierli et al. | 260/410.7 |
| 4,115,444 | 9/1978 | Rizkalla | 260/410.7 |
| 4,251,458 | 2/1981 | Pagach | 260/410.7 |
| 4,335,059 | 6/1982 | Rizkalla | 260/410.7 |
| 4,483,803 | 11/1984 | Rizkalla | 260/410.7 |
| 4,483,804 | 11/1984 | Rizkalla | 260/410.7 |
| 4,559,183 | 12/1985 | Hewlett | 260/410.7 |
| 4,698,187 | 10/1987 | Hewlett | 260/410.7 |

FOREIGN PATENT DOCUMENTS

| | | |
|---|---|---|
| 191217 | 8/1986 | European Pat. Off. . |
| 322027 | 6/1989 | European Pat. Off. . |
| 52-78813 | 7/1977 | Japan . |
| 64-19042 | 1/1989 | Japan . |

OTHER PUBLICATIONS

Chemical Abstracts, vol. 111, 1989, pp. 592, 172674z.
Menz. "Polmorphism of Diacid Triglycerides of the Stearic Acid & Behenic Acid Series", Fette Seifen Anstrichmittel, vol. 77, Issue 5 (1975), pp. 170–173.
Jackson et al., "Polymorphism of 1-Stearyl & 1-Palmityl-Diacetin, -Dibutyrin, -Dicaproin & 1-Stearyl-Dipropionin", J. Am. Chem. Soc., vol. 73 (1951), pp. 4827–4829.
Feuge et al., "Dilatometric Properties of Some Butyropalmitins, Butyrostearins and Acetopalmitins", J. Am. Oil Chem. Soc., vol. 33, 1956, pp. 367–371.
Gros et al, "Physical Properties of Aceto-and Butyro-Oleins, Mono-Olein, and DiOlein", J. Am. Oil Chem. Soc., vol. 34 (1957) pp. 239–244.
Feuge et al, "Modification of Vegetable Oils: Plasticity of Some Aceto Derivatives of Monostearin", J Am. Oil Chem. Soc., vol. 29 (1952), pp. 11–14.
Fuege, "Acetoglycerides-New Fat Products of Potential Value to the Food Industry", Food Technology (Jun. 1955), pp. 314–318.
Gruger et al, "Glycerolysis of Marine Oils and the Preparation of Acetylated Monoglycerides", J. Am. Oil Chem. Soc., vol. 37 (1960), pp. 214–217.
Mattson et al, "Esterification of Hydroxy Compounds by Fatty Acid Anhydrides", J. Lipid Res., vol. 5, No. 3 (1964), pp. 374–377.
Friedman et al, "Maleyl Esters of Monoglycerides of Saturated Fatty Acids", J. Am. Oil Chem. Soc., vol. 60, No. 6 (1983), pp. 1134–1140.
Lauridsen, "Food Emulsifiers: Surface Activity, Edibility, Manufacture, Composition, and Application", J Am. Oil Chem. Soc., vol. 53 (1976), pp. 400–407.
Van Haften, "Fat-Based Food Emulsifiers", J. Am. Oil Chem. Soc., vol. 56 (1979), pp. 831A–835A.
Hartman, "Preparation of α-Monoglycerides by Modified Isopropylidene–Glycerol Method", Chemistry and Industry (Jun. 18, 1960), pp. 711–712.
Mattson et al, "Synthesis and Properties of Glycerides", J. Lipid Res., vol. 3, No. 3 (1962), pp. 182–196.
Choudhury, "Prep. and Purification of Monoglycerides: Direct Esterification of Fatty Acids with Glycerol", J. Am. Oil Chem. Soc., vol. 39 (1962), pp. 345–347.
Holmberg, "Enzymantic Preparation of Monoglycerides in Microemulsion", J. Am. Oil Chem. Soc., vol. 65 (1988), pp. 1544–1548.
Choudhury, "The Preparation and Purification of Monoglycerides: Glycerolysis of Oils", J. Am. Oil Chem. Soc., vol. 37 (1960), pp. 483–486.
Feuge et al. "Modification of Vegetable Oils: the Practical Preparation of Mono-and Diglycerides", Oil and Soap, (Aug. 1946), pp. 259–264.
Ralston, Fatty Acids and Their Derivatives, (1948), pp. 794–803.
PCT Application 91/03944 to Givens et al, published Apr. 4, 1991.

*Primary Examiner*—Jose G. Dees
*Assistant Examiner*—Deborah D. Carr
*Attorney, Agent, or Firm*—Richard C. Witte; Ronald L. Hemingway; Eric W. Guttag

[57] ABSTRACT

A process for the selective esterification of long chain length fatty acid monoglycerides, particularly monobehenin, with medium chain length fatty acid anhdyrides, particularly a mixture of $C_8$ and $C_{10}$ saturated fatty acid anhdyrides is disclosed. In this process, an at least about 60% pure $C_{18}$–$C_{24}$ fatty acid monoglyceride or mixture thereof is esterified with an at least about 50% pure $C_6$–$C_{10}$ fatty acid anhydride or mixture thereof at a temperature of from about 90° to aobut 190° C. in the substantial absence of an esterificastion catalyst. The mole ratio of fatty acid anhydride to monoglyceride used in this monoglyceride esterification is at least about 2:1.

33 Claims, No Drawings

SELECTIVE ESTERIFICATION OF LONG CHAIN FATTY ACID MONOGLYCERIDES WITH MEDIUM CHAIN FATTY ACID ANHYDRIDES

TECHNICAL FIELD this application relates to a process for the selective esterification of long chain length fatty acid monoglycerides with medium chain length fatty acid anhydrides to provide reduced calorie fats. This application particularly relates to the esterification of monobehenin with a mixture of $C_8$ and $C_{10}$ saturated fatty acid anhydrides to provide a preferred reduced calorie confectionery fat.

European patent application 322,027 to Seiden, published Jun. 28, 1989, discloses reduced calorie fats comprising triglycerides having medium chain length ($C_6-C_{10}$) saturated fatty acid residues and long chain length (e.g., $C_{18}-C_{24}$) saturated fatty acid residues. These reduced calorie fats primarily comprise triglycerides selected from mono- long chain length MLM and MML triglycerides, and di- long chain length LLM and LML triglycerides, where M is a medium chain saturated fatty acid residue(s) and L is a long chain saturated fatty acid residue(s). These reduced calorie fats can be used as complete or partial replacement for other triglyceride fats to provide calorie reduction in various fat-containing food compositions such as salad oils, emulsified spreads, frozen desserts and the like.

For certain preferred reduced calorie fats, L is predominantly a long chain behenic fatty acid residue and M is a mixture of $C_8$ and $C_{10}$ saturated fatty acids. These preferred reduced calorie fats are useful as partial or complete replacements for confectionary fats, especially cocoa butter, particularly in chocolate-flavored products such as candy bars and enrobed chocolate-flavored products. To provide optimum mouthmelt properties for these preferred reduced calorie fats, the level of MML and MLM (mono-long chain) triglycerides combined is desirably maximized. e.g., to levels of about 90% or higher.

This European patent application 322,027 describes the synthesis of these reduced calorie fats by a wide variety of techniques. These techniques include: (a) random rearrangement of long chain triglycerides (e.g., tristearin or tribehenin) and medium chain triglycerides; (b) esterification of glycerol with a bland of the corresponding fatty acids; (c) transesterification of a blend of medium and long chain fatty acid methyl esters with glycerol; and (d) transesterification of long chain fatty acid glycerol esters (e.g., glyceryl behenate) with medium chain triglycerides. In particular, Example 1 of European patent application 322,027 discloses the synthesis of such reduced calorie fats by random rearrangement of tribehenin and commercial grade medium chain triglycerides using sodium methoxide as the catalyst at reaction temperatures of from 78° to 91° C. This catalyzed random rearrangement synthesis provides a complex mixture of MLM, MML, LML, LLM, MMM and LLL triglycerides, as well as the various mono- and diglycerides. (A similar, complex mixture of triglycerides is obtained when glycerol is esterified with a mixture of medium and long chain fatty acids, in the absence of an esterification catalyst, at temperatures of about 265° C.). Of this complex mixture, the particularly desirable MML/MLM triglycerides comprise, at most. only about 40 to about 45% of the total triglycerides. This necessitates an extensive purification step by techniques such as molecular distillation, solvent fractional crystallization, winterization or a combination of such techniques, to increase the level of desired MML/MLM triglycerides in the reduced calorie fat.

Menz, "Polymorphism of Diacid Triglycerides of the Stearic Acid and Behenic Acid Series," *Fette Seifen Anstrichmittel*, Vol. 77, Issue 5 (1975), pp. 170-73, discloses the selective esterification of 1-monostearin and 1-monobehenin with short/medium chain ($C_2-C_8$) saturated fatty acid chlorides in pyridine. See also Jackson et al, "The Polymorphism of 1-Stearyl and 1-Palmityl-Diacetin, -Dibutyrin-Dicaproin and 1-Stearyl Dipropionin," *J. Am. Chem. Soc.*, Vol 73 (1951), pp. 4827-29, which discloses the selective esterification of 1-monostearin or 1-monopalmitin with the respective fatty acid chlorides of acetic acid, butyric acid or caproic acid. The fatty acid chlorides used in the Menz and Jackson et al processes are extremely expensive, particularly in synthesizing MML/MLM triglycerides on a commercial scale. In addition, these fatty acid chlorides are extremely toxic and generate undesirable reaction by-products during esterification that need to be removed prior to use of the MML/MLM triglycerides in food applications. Accordingly, it would be desirable to have a process for selectively obtaining MML/MLM triglycerides which uses less expensive acylating materials that eliminate the generation of by-products known to be undesirable, without the use of esterification catalysts or solvents.

BACKGROUND ART

A. Random Rearrangement of Tribehenin and Medium Chain Triglycerides

European patent application 322,027 to Seiden, published Jun. 28, 1989, discloses the preparation of a complex mixture of MML, MLM, LML, MLL, LLL and MMM triglycerides by random rearrangement of tribehenin and commercial grade medium chain triglycerides using sodium methoxide as the catalyst at reaction temperatures of from 78°-91° C. See Example 1.

B. Esterification of 1-Monobehenin and 1-Monostearin with Short/Medium Chain Fatty Acid Chlorides Menz, "Polymorphism of Diacid Triglycerides of the Stearic Acid and Behenic Acid Series," *Fette Seifen Anstrichmittel*, Vol. 77, Issue 5 (1975), pp. 170-73, discloses a study of the polymorphic properties of 1-monostearin and 1-monobehenin which have been esterified with $C_2$, $C_4$, $C_6$ or $C_8$ short/medium chain saturated fatty acid chlorides in pyridine.

Jackson et al, "The Polymorphism of 1-Stearyl and 1-Palmityl-Diacetin, - Dibutyrin-Dicaproin and 1-Stearyl Dipropionin," *J. Am. Chem. Soc.*, Vol. 73 (1951), pp. 4827-29, discloses the polymorphism of 7 unsymmetrical triglycerides obtained by esterifying 1-monostearin or 1-monopalmitin with the respective fatty acid chlorides of acetic acid, butyric acid or caproic acid. See also Feuge et al, "Dilatometric Properties of Some Butyropalmitins, Butyrostearins, and Acetopalmitins," *J. Am. Oil Chem. Soc.*, Vol. 33, 1956, pp. 367-71, for a similar disclosure.

C. Esterification of 1-Monoglycerides with Acetic Anhydride

Japanese Laid-Open Patent Application 52-78813 to Sato et al, published Jul. 2, 1977, monoglycerides (including 1-monoglycerides) or diglycerides with acetic anhydride using sodium acetate anhydride or pyridine as the catalyst. The long chain fatty acid glycerides esterified according to this process can have chain lengths ranging from $C_{10}$ t $C_{20}$. Preferred glycerides used in this reaction are derived from saturated fatty acids such as stearic or palmitic acid, or unsaturated fatty acids such as oleic or linoleic acid. A slight mole excess of acetic anhydride (e.g., 3:1 mole ratio of anhydride to monoglyceride) is used in this reaction which can be carried out at temperatures of from 80°-130° C. (e.g., 110° C.) for 0.5 to 2 hours (e.g., 1 hour).

Feuge et al, "Modification of Vegetable Oils: Plasticity of Some Aceto Derivatives of Monostearin", *J. Am. Oil Chem. Soc.*, Vol. 29 (1952), pp. 11-14, discloses the preparation of acetoglycerides from 1-monostearin. This reaction consists of mixing the 1-monostearin with acetic anhydride in a mole ratio of 1:0.5 to 1:2 for about 1 hour at 110° C., followed by hydrolysis of the unreacted acetic anhydride and water washing to remove acetic acid that has been generated during the reaction. See also Feuge, "Acetoglycerides - New Fat Products of Potential Value to the Food Industry", *Food Technology* (June 1955), pp. 314-18 (similar disclosure); Gruger et al, "Glycerolysis of Marine Oils and the Preparation of Acetylated Monoglycerides", *J. Am. Oil Chem. Soc.*, Vol. 37 (1960), pp. 214-217 (acetylation of 1-monoglycerides derived from marine oils using a slight mole excess of acetic anhydride at a reaction temperature of 140° C. for 1 hour).

DISCLOSURE OF THE INVENTION

The present invention relates to a process for selectively making MML/MLM triglycerides that are useful as reduced calorie fats, wherein M is a $C_6$-$C_{10}$ fatty acid residue or mixture thereof, and L is a $C_{18}$-$C_{24}$ fatty acid residue or mixture thereof, and preferably MML/MLM triglycerides that are useful as reduced calorie confectionery fats, wherein M is a mixture of $C_8$ and $C_{10}$ saturated fatty acid residues, and L is at least about 90% behenic fatty acid residues. In this process, an at least about 60% pure $C_{18}$-$C_{24}$ fatty acid monoglyceride or mixture thereof is esterified with an at least about 50% pure $C_6$-$C_{10}$ fatty acid anhydride or mixture thereof at a temperature of from about 90° to about 190° C. in the substantial absence of an esterification catalyst. The mole ratio of fatty acid anhydride to monoglyceride used in this monoglyceride esterification is at least about 2:1.

The monoglyceride esterification process of the present invention has a number of significant advantages over prior random rearrangement synthesis processes and acid chloride esterification processes. The monoglyceride esterification process of the present invention is relatively fast, is highly selective in obtaining MML/MLM triglycerides (e.g. with purities as high as from about 88 to about 98%), and typically goes essentially to completion (i.e., at least about 99% of the partial glycerides are converted to triglycerides). As a result, the subsequent purification step to further increase the level of MML/MLM triglycerides is not as extensive, and may not even be required in certain cases. In addition, the monoglyceride esterification process of the present invention uses fatty acid anhydride starting materials that eliminate the generation of known, undesired by-products, such as difatty ketones. Also, esterification catalysts and solvents are not required, or even desired, in the process of the present invention. Other advantages of this monoglyceride esterification process include better color in the resulting MML/MLM triglyceride product, and no disproportionation of the monoglyceride starting materials.

A. Definitions

By "medium chain fatty acid," as used herein, is meant a saturated fatty acid, unsaturated fatty acid, or mixture thereof, having 6 to 10 carbon atoms.

By "medium chain fatty acid anhydride" as used herein, is meant the dehydration product of two medium chain fatty acids.

By "medium chain saturated fatty acid," as used herein, is meant $C_6$ (caproic), $C_8$ (caprylic), or $C_{10}$ (capric) saturated fatty acids, or mixture thereof. The $C_7$ and $C_9$ saturated fatty acids are not commonly found, but they are not excluded from the possible medium chain fatty acids. The present medium chain fatty acids do not include lauric acid ($C_{12}$), sometimes referred to in the art as a medium chain fatty acid.

By "long chain fatty acid," as used herein, is meant a saturated fatty acid, unsaturated fatty acid, or mixture thereof, having 18 to 24 carbon atoms.

By "long chain saturated fatty acid," as used herein is meant $C_{18}$ (stearic), $C_{19}$ (nonadecylic), $C_{20}$ (arachidic), $C_{21}$ (heneicosanoic), $C_{22}$ (behenic), $C_{23}$ (tricosanoic), or $C_{24}$ (lignoceric) saturated fatty acids, or mixtures thereof.

By "MML," as used herein, is meant a triglyceride containing a long chain fatty acid residue in the #1 or #3 position (an end position) with two medium chain fatty acid residues in the remaining two positions, while "MLM" represents a triglyceride with a long chain fatty acid residue in the #2 position (the middle position) and two medium chain fatty acid residues in the #1 and #3 positions. Similarly, "MML" represents a triglyceride with a medium chain fatty acid residue in the #1 or #3 position and two long chain fatty acid residues in the remaining two positions, "LML" represents a triglyceride with a medium chain fatty acid residue in the #2 position and two long chain fatty acid residues in the #1 and #3 positions, "MMM" represents a triglyceride containing medium chain fatty acid residues at all three positions, and "LLL" represents a triglyceride containing long chain fatty acid residues at all three positions.

By "the level of MML/MLM triglycerides" is meant the combined level of MML and MLM triglycerides.

By "long chain fatty acid monoglyceride" is meant a monoglyceride which contains one long chain fatty acid residue in the #1 position (i.e., a 1-monoglyceride) or the #2 position (i.e., a 2-monoglyceride).

As used herein, the term "comprising" means various components or steps can be conjointly employed in the present invention. Accordingly, the term "comprising" encompasses the more restrictive terms "consisting essentially of" and "consisting of."

All percentages, ratios and proportions used herein are by weight unless otherwise specified.

B. Sources of Medium Chain Fatty Acid Anhydrides

The source of medium chain ($C_6$-$C_{10}$) fatty acid anhydridees used in the monoglyceride esterification process of the present invention needs to be of sufficiently high purity to provide the desired level of MML/MLM triglycerides. Generally the source of medium chain fatty acid anhydrides is at least about 50% pure in medium chain fatty acid anhydrides, with up to about 50% of the balance typically being medium chain fatty acids.

(Due to the very fast acylation rate of anhydrides versus acids, the medium chain fatty acids are essentially an inert diluent.) Preferably, the source of medium chain fatty acid anhydrides is at least about 70% pure in such fatty acid anhydrides, with up to about 30% of the balance typically being medium chain fatty acids. Preferably, the source of medium chain fatty acid anhydrides comprises $C_8$ saturated fatty acid anhydride, $C_{10}$ saturated fatty acid anhydride, or a mixture of $C_8$ and $C_{10}$ saturated fatty acid anhydrides. The weight ratio of $C_8$ to $C_{10}$ saturated fatty acid anhydrides is preferably in the range of from about 30:70 to about 45:55.

The medium chain fatty acid anhydrides useful in the present invention can be derived from a number of different sources. For example, medium chain fatty acid anhydrides can be obtained commercially from Sigma Aldrich Chemicals of St. Louis, Mo. They can also be synthesized from acetic or propionic anhydride. See U.S. Pat. No. 2,520,139 to Fuchs, issued Aug. 29, 1950; U.S. Pat. 2,411,567 to Fisher, issued Nov. 26, 1946; and Ralston, *Fatty Acids and Their Derivatives*, (1948), pp. 794–803, which are all incorporated by reference. See also U.S. Pat. No. 4,002,677 Naglierli et al, issued Jan. 11, 1977; U.S. Pat. No. 4,002,678 to Naglierli et al, issued Jan. 11, 1977; U.S. Pat. No. 4,115,444 to Rizkalla, issued Sep. 19, 1978; U.S. Pat. No. 4,251,458 to Pagach, issued Feb. 11, 1981; U.S. Pat. No. 4,335,059 to Rizkalla, issued Jun. 15, 1982; U.S. Pat. No. 4,483,803 to Rizkalla, issued Nov. 20, 1984; U.S. Pat. No. 4,483,804 to Rizkalla, issued Nov. 20, 1984; U.S. Pat. No. 4,559,183 to Hewlett, issued Dec. 17, 1985; U.S. Pat. No. 4,698,187 to Hewlett, issued Oct. 6, 1987; all of which are incorporated by reference, for other processes for synthesizing medium chain fatty acid anhydrides.

The medium chain fatty acid anhydrides useful in the present invention are usually prepared by admixing the corresponding medium chain fatty acids with a stoichiometric amount or excess of acetic or propionic anhydride, followed by separation of the desired medium chain fatty acid anhydrides from the resulting reaction mixture. A preferred synthesis for preparing these medium chain fatty acid anhydrides involves metathesis with acetic anhydride either at low temperatures (e.g., 0° to 60° C.) using strong acid catalysts (e.g., perchloric acid), or at high temperatures (e.g., from 120° to 175° C.) without the use of strong acid catalysts, but with volatilization or stripping of the acetic acid formed during the reaction. This metathesis reaction can generally be represented by the following equation:

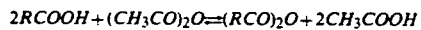
$$2RCOOH + (CH_3CO)_2O \rightleftharpoons (RCO)_2O + 2CH_3COOH$$

where R is the residue of the medium chain fatty acid.

Typically, the medium chain fatty acid is heated with a 0 to 200% mole excess of acetic anhydride under reflux to effect this metathesis reaction. The acetic acid formed, plus any residual unreacted acetic anhydride, is distilled off at temperature of from 140° to 175° C., and at atmospheric pressure. Alternatively, a moderate vacuum (e.g., 200 mm. Hg), or inert gas (e.g., nitrogen) can be used to effect this separation. This metathesis reaction can be conducted in either batch or continuous reaction/stripping systems. When stoichiometric amounts of acetic anhydride are used, the reaction mixtures obtained typically comprise from about 60 to about 80% symmetrical (e.g., $C_8/C_8$, $C_{10}/C_{10}$ or $C_8/C_{10}$) fatty acid anhydrides, from about 15 to about 30% fatty acids, and from about 5 to about 10% mixed, asymmetrical (e.g., $C_2/C_8$ or $C_2/C_{10}$) fatty acid anhydrides.

Any asymmetrical fatty acid anhydrides that are present in the reaction mixture are unstable at temperatures above about 200° C., and are therefore readily converted to symmetrical fatty acid anhydrides by high temperature distillation (e.g., for 15 minutes at 205°–225° C. and at reduced pressure). Distillation is continued until the residual levels of the combined acetic impurities (e.g., acetic acid, acetic anhydride and asymmetrical fatty acid anhydrides containing acetyl ($C_2$) groups) are reduced to about 0.5% or less, preferably to about 0.1% or less. This reduction in acetic impurities is necessary to prevent undesirable acetin fats from being formed during subsequent esterification.

The completeness of the above metathesis reaction is a function of reaction time and acetic anhydride level. As a result, the ultimate yield of the desired medium chain fatty acid anhydrides is achieved in very short reaction times, and is not changed unless the equilibrium is shifted by removal of the medium chain fatty acid anhydrides or acetic acid formed. The ultimate yield of medium chain fatty acid anhydride is primarily determined by the amount of excess acetic anhydride used. This ultimate yield reaches a level of from 85 to 95% when a from 50 to 100% mole excess of acetic anhydride is used. This ultimate yield can be increased to from 95 to 98% by using a from 100 to 200% mole excess of acetic anhydride.

While this metathesis reaction is primarily directed at the preparation of medium chain *saturated* fatty acid anhydrides, no particular problems are encountered in using this reaction to prepare medium chain *unsaturated* fatty acid anhydrides. By contrast, the preparation of unsaturated acid chlorides can be difficult since the chloride used in the acid chloride synthesis tends to react at the unsaturated position(s). This ease of preparation of medium chain unsaturated fatty acid anhydrides is an important advantage of the esterification process of the present invention compared to prior acid chloride esterification methods.

The medium chain fatty acids used to prepare the respective anhydrides can be derived from a number of different sources. For example, medium chain saturated fatty acids can be obtained from coconut, palm kernel or babassu oils. They can also be obtained from commercial medium chain triglycerides, such as the Captex 300 brands sold by Capitol City Products of Columbus, Ohio. Typically, these sources of medium chain fatty acids are subjected to hydrolysis to provide a mixture of free fatty acids, followed by solventless fractionation to provide a fatty acid fraction enriched in the medium chain fatty acids. For example, refined, bleached and deodorized coconut or palm kernel oil, which has been hydrogenated to further increase the level of saturated fatty acids, can be subjected to hydolysis conditions, followed by solventless fractionation (i.e., distillation) to provide a fatty acid fraction enriched in a mixture of $C_8$ and $C_{10}$ saturated fatty acids that is typically processed to meet Food Chemical Codex criteria for caprylic ($C_8$) and capric ($C_{10}$) acids. It is also desirable that the sources of medium chain fatty acids have good thermal color stability, e.g., after heating at 205° C. for two hours, a mixture of $C_8$ and $C_{10}$ saturated fatty acids has only a 5–10% optical transmission reduction when measured at 440/550 nanometers. The source of medium chain fatty acids also need to be of sufficiently high purity in order to be useful in the preparation of the respective medium chain fatty acid anhydrides. Generally, the source of medium chain fatty acids is at least about 90% pure in medium chain fatty acids, and is preferably at least about 95% pure in such acids.

It should be noted that purification of the medium chain fatty acids can be readily accomplished by conventional distillation techniques. Accordingly, the resultant medium chain fatty acid anhydrides are essentially colorless and odor free. By contrast, purification of long chain fatty acid anhydrides typically requires crystallization from organic solvents (e.g., behenic anhydrides are typically crystallized from benzene or chloroform) due to the very high boiling point of these anhydrides. Materials processed with such organic solvents are not readily made food compatible. Accordingly, the use of medium chain fatty acid anhydrides according to the present invention is advantageous in the preparation of food grade MML/MLM triglycerides compared to the use of long chain fatty acid anhydrides.

C. Sources of Long Chain Fatty Acid Monoglycerides

The long chain (i.e., $C_{18}$–$C_{24}$) fatty acid monoglycerides used in the monoglyceride esterification process of the present invention can be prepared by a wide variety of techniques. These techniques include:

(a) Esterification or transesterification of glycerol acetone or glycidol with the respective long chain fatty acid(s), or long chain fatty acid lower alkyl (e.g., methyl or ethyl) ester(s), followed by hydrolysis of the respective blocking group. See Hartman, "Preparation of α-Monoglycerides by a Modified Isopropylidene-Glycerol Method," *Chemistry and Industry* (Jun. 18, 1960), pp. 711-12 (herein incorporated by reference), which discloses the preparation of 1-monoglycerides by the use of the modified isopropylidene-glycerol method, and Mattson et al, "Synthesis and Properties of Glycerides," *J. Lipid Res.*, Vol. 3, No. 3 (1962), pp. 281-96 (herein incorporated), which discloses the same method. See also U.S. Pat. No. 3,595,888 to Reiser et al, issued Jul. 27, 1971, and U.S. Pat. No. 3,251,870 to Dalby, issued May 17, 1966 (herein incorporated by reference) which disclose isopropylidene-glycerol and glycidol methods for synthesizing 1-monoglycerides.

(b) Esterification or transesterification of glycerol with the respective long chain fatty acid(s), or long chain fatty acid lower alkyl ester(s), optionally using strong base esterification catalysts such as sodium hydroxide or sodium methoxide, or strong acid esterification catalysts such as hydrogen fluoride, perchloric acid, phosphoric acid or p-toluenesulfonic acid. See Choudhury, "The Preparation and Purification of Monoglycerides: Direct Esterification of Fatty Acids with Glycerol", *J. Am. Oil Chem. Soc.* Vol. 39 (1962), pp. 345-47 (herein incorporated by reference), which discloses the preparation of 1-monoglycerides by esterification of glycerol with various fatty acids (e.g. stearic acid), optionally using sodium hydroxide as the catalyst. See also U.S. Pat. No. 3,551,464 to Miller et al, issued Dec. 29, 1970 (herein incorporated by reference), which discloses the preparation of monoglycerides from long chain aliphatic acids and esters that are esterified or transesterified with glycerol using hydrogen fluoride as the catalyst.

(c) Hydrolysis of a naturally occurring oil, preferably a completely or substantially completely hydrogenated naturally occurring oil (e.g., high erucic acid rapeseed oil or soybean oil hydrogenated to an Iodine Value (I.V.) of about 10 or less) by the use of a 1,3-specific lipase, followed by removal of the residual fatty acids, glycerol, diglycerides and triglycerides. See Holmbey, "Enzymatic Preparation of Monoglycerides in Microemulsion," *J. Am. Oil Chem. Soc.*, Vol. 65 (1988), pp. 1544-48, which is incorporated by reference.

(d) Esterification or transesterification of glycerol with the respective long chain fatty acid(s) or long chain fatty acid lower alkyl ester(s) using a monoglyceride lipase (e.g., Ammano Pharmaceutical type G), followed by purification. See European patent application 191,217 to Yamaguchi et al, published Aug. 20, 1986, which is incorporated by reference.

(e) Glycerolysis of naturally occurring oils, preferably completely or substantially completely hydrogenated naturally occurring oils. See Choudhury, "The Preparation and Purification of Monoglycerides; Glycerolysis of Oils", *J. Am. Oil Chem. Soc.*, Vol. 37 (1960), pp. 483-86, and Feuge et al, "Modification of Vegetable Oils: The Practical Preparation of Mono- and Diglycerides," Oil and Soap, (August 1946), p. 259-64, which are incorporated by reference.

The long chain fatty acids per se or naturally occurring fats and oils can serve as sources of the long chain saturated fatty acids. For example, soybean oil and high erucic acid rapeseed oil hydrogenated to an I.V. of about 10 or less are good sources of stearic and behenic fatty acids, respectively. Odd chain length long chain fatty acids can be derived from certain marine oils. Alternatively, mixed chain length fatty acid monoglycerides can be fractionated to provide a source of long chain fatty acids. For example, hydrogenated high erucic acid rapeseed oil can be transesterified with glycerol to provide a mixture of long chain fatty acid monoglycerides which can be subsequently fractionated by liquid/liquid extraction or absorptive separation to yield a monobehenin-enriched mixture. The source of long chain fatty acids usually needs to be of sufficiently high purity in order to provide monoglycerides suitable for the esterification process of the present invention. Usually, the source of long chain fatty acids is at least about 90% pure, preferably at least about 95% pure, most preferably at least about 98% pure, in long chain fatty acids. Preferably, the purity is in the range of from about 90 to about 98% long chain saturated fatty acids.

For the esterification process of the present invention, the source of long chain fatty acid monoglycerides needs to be of sufficiently high purity in order to provide the desired level of MML/MLM triglycerides. Generally, the source of these monoglycerides needs to be at least about 60% pure, preferably at least about 90% pure, more preferably at least about 95% pure, most preferably at least about 98% pure, in long chain fatty acid monoglycerides. Such purities can typically be achieved by purification of the crude source of monoglycerides by molecular distillation, fractional crystallization, liquid/liquid extraction or adsorptive separation, e.g., by weak acid ion exchange resins to remove various impurities, including unreacted long chain fatty acids and, particularly, to decrease the level of dilong chain fatty acid diglycerides (LL) to about 3% or less, preferably about 1% or less. Residual glycerol present in the crude source of monoglycerides can be removed by settling, centrifugation, thermal distillation, or fractional crystallization to decrease the glycerol level to about 1% or less, preferably about 0.5% or less. In addition, it is desirable to minimize the formation of glycerol dehydration products (e.g., polyglycerols) to a level of about 1% or less, preferably about 0.5% or less.

The preferred source of monoglycerides for use in the esterification process of the present invention is at least about 90%, preferably at least about 95%, and most preferably at least about 98%, pure monobehenin. This preferred monoglyceride can be obtained by hydrolysis of substantially completely hydrogenated (i.e., I.V. about 10 or less) high erucic acid rapeseed oil, solventless fractionation of the resulting fatty acid mixture to provide a behenic fatty acid-enriched fraction, and then esterification of glycerol with this behenic acid-enriched fraction to provide a crude mixture of monoglycerides. This crude monoglyceride mixture can be subsequently purified by molecular distillation, solvent (e.g., ethyl alcohol) crystallization, liquid/liquid extraction or adsorption on a weak acid ion exchange resin to yield a source of monoglycerides having the desired purity monobehenin.

D. Esterification of Monoglycerides with Medium Chain Fatty Acid Anhydrides

The desired MML/MLM triglycerides are made according to the process of the present invention by the esterification of the long chain fatty acid monoglycerides described in part C of this application with the medium chain fatty acid anhydrides described in part B of this application. A particularly important aspect of this esterification process is to use an excess of the medium chain fatty acid anhydrides relative to the monoglycerides, i.e. a mole ratio of fatty acid anhydride to monoglyceride of at least about 2:1. Surprisingly, it has been found that a greater than stoichiometric amount of fatty acid anhydride relative to the monoglyceride is required to obtain higher levels of MML/MLM triglycerides. For example, sequential addition of the medium chain fatty acid anhydride to first convert the monoglyceride to the diglyceride, and then to convert the diglyceride to the triglyceride, results in lower levels of MML/MLM triglycerides. Typically, the mole ratio of fatty acid anhydride to monoglyceride is in the range of from about 2:1 to about 5:1, with a preferred mole ratio in the range of from about 2:1 to about 3:1. Mole ratios higher than about 5:1 can be used in this esterification process, but are usually not desirable since this results in a significant amount of unreacted fatty acid anhydride that needs to be removed during subsequent purification and does not significantly increase the level of desired MML/MLM triglycerides.

Another important aspect of the esterification process of the present invention is that it is typically carried out in a solvent-free system. At the temperatures at which the esterification process is carried out, the mixture of monoglycerides and medium chain fatty acid anhydrides forms an essentially homogeneous melt. Accordingly, solvents are not required in carrying out the esterification process of the present invention.

Another important aspect of the esterification process of the present invention is that it is carried out in the substantial absence of an esterification catalyst. As used herein, the term "substantial absence of esterification catalyst" means that the esterification process of the present invention is carried out without intentionally adding such catalysts. Esterification catalysts such as strong bases (e.g. pyridine or alkyl substituted pyridine derivatives such as N,N-dimethyl 1,4-aminopyridine) and strong acids (e.g. sulfuric acid or perchloric acid) are not required in order to carry out the esterification process of the present invention. Indeed, in the case of esterification reactions involving medium chain unsaturated fatty acid anhydrides, long chain unsaturated fatty acid monoglycerides, or both, the use of chlorinated acid catalysts (e.g., perchloric acid) is highly undesirable due to the tendency of the chloride ions to react with the double bond(s).

Another important aspect of the esterification process of the present invention is the esterification temperatures used. Surprisingly, it has been determined that, at esterification temperatures of about 190° C. or less, the esterification of monoglycerides with medium chain fatty acid anhydrides occurs without rearrangement of the long chain fatty acid residues attached to the glyceride. The esterification of monoglycerides with medium chain fatty acid anhydrides according to the process of the present invention is preferably carried out in the substantial absence of water, i.e. this esterification is preferably carried out in a substantially anhydrous system, to avoid converting the anhydrides to the respective fatty acids. Because the esterification system is substantially free of water, the rearrangement of long chain fatty acid residues attached to the glyceride due to hydrolysis/reesterification is substantially reduce. Accordingly, the esterification process of the present invention is "selective" in converting the monoglycerides to the desired MML/MLM triglycerides.

With this guideline in mind, the esterification process of the present invention can be carried out over a fairly wide range of temperatures. Generally, the esterification of the monoglycerides with the medium chain fatty acid anhydrides can be carried out at a temperature in the range of from about 90° to about 190° C. Preferably, the esterification of the monoglycerides with the medium chain fatty acid anhydrides is carried out at a temperature in the range of from about 120° to about 160° C. This preferred range is particularly desirable in esterifying the preferred monobehenin monoglycerides with $C_8/C_{10}$ saturated fatty acid anhydrides.

The esterification process of the present invention can be carried out as either a batch or continuous reaction system. For example, plug or mixed flow configurations can be used to continuously react the medium chain fatty acid anhydrides with the monoglycerides in one or more stages. Alternatively, thin film-type reaction systems operated at higher temperatures with short residence times can be used in this esterification step. Typically, the solid or liquid monoglycerides are added to the melted medium chain fatty acid anhydrides at the desired esterification temperature to minimize disproportionation of the monoglycerides to diglycerides/glycerol, as well as the reaction of monoglycerides with medium and long chain (ML) diglycerides. The monoglycerides are also typically added slowly to the melted fatty acid anhydrides at a controlled rate of addition during the esterification to minimize the concentration of unreacted monoglycerides in the mixture (e.g., to about 0.2% or less), and thus minimize the formation of MLL/LML triglycerides. The reactants, in particular the monoglycerides, are also preferably dry (substantially anhydrous) to avoid converting the anhydrides to the respective fatty acids. The esterification process is also preferably carried out under an inert gas atmosphere (e.g., nitrogen) to prevent moisture pickup and to maintain good color in the resulting esterified products.

The particular reaction times for carrying out this esterification process can vary greatly depending upon the mole ratio of fatty acid anhydride to monoglycerides used, the particular esterification temperatures used, and the yield/degree of purity desired for the MML/MLM triglycerides. Usually, reaction times of from about 0.5 to about 6 hours are suitable for batch reaction systems. Preferably, the esterification process of the present invention is carried out for a period of from about 1 to about 3 hours in a batch reaction system. (Equivalent residence times can be used in continuous reaction systems.)

An important result of the esterification process of the present invention is that typically at least 99% of the partial glycerides are converted to the respective triglycerides. Tin prior esterification reactions involving fatty acids and glycerol, it is difficult to achieve such conversions. For example, prior esterification reactions involving fatty acids and glycerol typically result in a residual level of diglycerides on the order of about 2 to 3%. The presence of such a high level of diglycerides can potentially cause bloom formation if the MML/MLM triglycerides are used in flavored confectionery fat products, thus requiring extensive purification such as by solvent fractionation or resin absorbents to decrease the level of such triglycerides. By contrast, the esterification process of the present invention can achieve very low diglyceride levels, e.g., diglyceride levels of about 1% or less. This makes the MML/MLM triglycerides obtained by the esterification process of the present invention particularly suitable for flavored confectionery fat products.

E. Purification to Increase the Level of MML/MLM Triglycerides

After the esterification process described in part D of this application has been carried out for the appropriate time, the level of desired MML/MLM triglycerides in the reaction mixture is usually at least about 55%, and is typically at least about 85%, more typically at least about 95%, when using preferred esterification conditions and high purity fatty acid anhydrides and monoglycerides. The particular level of MML/MLM triglycerides present in the reaction mixture will depend upon a number of factors, including the purity of the medium chain fatty acid anhydride and monoglyceride starting materials, and the reaction conditions use. For example, the esterification of at least about 90% pure monobehenin monoglyceride with an at least about 50% pure mixture of $C_8$ and $C_{10}$ saturated fatty acid anhydrides in a mole ratio of fatty acid anhydride to monoglyceride in the range of from about 2:1 to about 3:1 at a reaction temperature in the range of from about 120° to about 160° C. for from about 1 to about 6 hours typically results in a reaction mixture containing a level of from about 88% to about 98% MML/MLM triglycerides.

The level of MML/MLM triglycerides in this reaction mixture can be sufficiently high so that further purification is unnecessary, particularly depending upon the proposed use of the MML/MLM triglycerides. However, purification of the reaction mixture resulting from the esterification step is typically required in order to remove various components such as medium chain fatty acids generated during the reaction, and, in particular, MMM and MLL/LML triglycerides, as well as residual medium chain fatty acid anhydrides.

Subsequent purification can be carried out by a variety of techniques, or combinations of techniques. Residual fatty acid anhydrides can be converted to the respective fatty acids by the addition of water and then heating at 100° C. for 15 to 30 minutes. Alternatively, the anhydrides can be removed along with any residual medium chain fatty acids. The fatty acids can be removed by precipitation as salts (e.g., by addition of a base such as potassium carbonate). Both the fatty acids and anhydrides can be removed by the use of reverse osmosis membranes (e.g., NIRO HR98 polyamid/polysulfone thin film composite membranes having a 200–400 molecular weight cutoff), by flash evaporation, by steam stripping, or by vacuum distillation, to decrease the combined level of fatty acids/anhydrides in the reaction mixture to about 2% or less (as oleic acid). MMM triglycerides, and any residual fatty acids/anhydrides, can be removed by, for example, flash evaporation, evaporation using a wiped film evaporator (e.g., at temperatures of 200° to 240° C. and at pressures of 0.1–0.5 mm. Hg), molecular distillation (e.g., at 180°–225° C. and 1–20 microns pressure preferably with the fatty acids/anhydrides/MMM triglycerides as the distillate fraction), or by fractional crystallization using acetone, ethanol, methanol or hexane as the solvent, to decrease the level of MMM triglycerides in the reaction mixture to about 3% or less, and the level of residual fatty acids/anhydrides to about 0.5% or less (as oleic acid). MLL/LML triglycerides can be separated from the MML/MLM triglycerides by, for example, molecular distillation (e.g., at 200°–250° C. and 5–20 microns pressure, preferably with the desired MML/MLM triglycerides as the distillate fraction), solventless fractional crystallization (e.g., at 80° F. to promote crystal growth, followed by 70°–75° F. filtration), or solvent fractional crystallization using acetone, ethanol, methanol or hexane as the solvent, to decrease the level of combined MLL/LML triglycerides in the reaction mixture to about 3% or less. Surprisingly, the reaction mixture, which typically contains free fatty acids, is thermally stable, e.g., heating the reaction mixture for 1 hour at 240° C. does not cause significant rearrangement. Accordingly, a variety of thermal techniques can be used to purify the reaction mixture.

Any fatty acids, fatty acid anhydrides, MMM triglycerides or MLL/LML triglycerides removed during purification can be recycled to provide sources of medium chain fatty acid anhydrides or long chain fatty acid monoglycerides for further esterification according to the process of the present invention. Alternatively, these materials can be reincorporated into the esterification mixture at low levels for subsequent reaction to provide additional MML/MLM triglycerides. The purified mixture of MML/MLM triglycerides can also be subjected to bleaching and deodorizing steps for color and flavor/aroma improvement using conventional techniques well known in the fats and oils art. Alternatively, the reaction mixture can be bleached using conventional bleaching earth and/or activated carbon prior to purification. In the case of MML/MLM triglycerides which have unsaturated fatty acid residues or mixtures of unsaturated and saturated fatty acid residues, the MML/MLM triglycerides can be hydrogenated, before or after purification, to convert the unsaturated fatty acid residues to saturated fatty acid residues.

F. Uses of MML/MLM Triglycerides as Reduced Calorie Fats

The MML/MLM triglycerides obtained according to the present invention (where L is a long chain *satu-*

*rated* fatty acid residue and M is a medium chain *saturated* fatty acid residue) can be used as reduced calorie fats to partially or totally replace normal triglyceride fat in any fat-containing food composition comprising fat and nonfat ingredients to provide reduced calorie benefits. In order to obtain a significant reduction in calories, it is necessary that at least about 50% of the total fat in the food composition, or at least about 20% of the caloric value of the food, comprise the reduced calorie fat. On the other hand, very low calorie and thus highly desirable food compositions are obtained when the total fat comprises up to 100% of the reduced calorie fat, and up to about 50% of the calories.

The present reduced calorie fats are useful in a wide variety of food and beverage product. For example, the fats can be used in the production of baked goods in any form, such as mixes, shelf-stable baked goods, and frozen baked goods. Possible applications include, but are not limited to, cakes, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, baked farinaceous snack foods, and other baked salted snacks.

In addition to their uses in baked goods, the reduced calorie fats can be used alone or in combination with other regular calorie fats and oils to make shortening and oil products. Suitable sources of regular fats and oils include, but are not limited to: 1) vegetable fats and oils such as soybean, corn, sunflower, rapeseed, low erucic acid rapeseed, canola, cottonseed, olive, safflower, and sesame seed; 2) meat fats such as tallow or lard; 3) marine oils; 4) nut fats and oils such as coconut, palm, palm kernel, or peanut; 5) milkfat; 6) cocoa butter and cocoa butter substitutes such as shea, or illipe butter; and 7) synthetic fats. Shortening and oil products include, but are not limited to, shortenings, margarines, spreads, butter blends, lards, salad oils, popcorn oils, salad dressings, mayonnaise, and other edible oils.

Certain of the present reduced calorie fats are especially useful in flavored confectionery composition, particularly chocolate-flavored confectionery compositions. See U.S. application Ser. No. 329,619 to Albert M. Ehrman, Paul Seiden, Rose M. Weitzel and Robert L. White, (P&G Case 3948), filed Mar. 28, 1989, which is incorporated by reference. These flavored confectionery compositions comprise:

a. a flavor enhancing amount of a flavor component;
b. from about 25 to about 45% of a fat component comprising:
  (1) at least about 70% of a reduced calorie fat having:
    (a) at least about 85% combined MLM and MML triglycerides;
    (b) no more than about 5% combined LLM and LML triglycerides;
    (c) no more than about 2% LLL triglycerides;
    (d) no more than about 4% MMM triglycerides;
    (e) no more than about 7% other triglycerides; wherein M is a $C_6$ to $C_{10}$ saturated fatty acid residue and L is a $C_{20}$ to $C_{24}$ saturated acid residue;
    (f) a fatty acid composition having:
      (i) from about 40 to about 60% combined $C_8$ and $C_{10}$ saturated fatty acids,
      (ii) a ratio of $C_8$ to $C_{10}$ saturated fatty acids of from about 1:2.5 to about 2.5:1,
      (iii) from about 40 to about 60% behenic fatty acid,
  (2) up to about 15% milkfat;
  (3) up to about 20% cocoa butter;
  (4) no more than about 4% diglycerides; and
c. from about 55 about 75% other nonfat confectionery ingredients.

These compositions are preferably tempered according to the process disclosed in said Ehrman et al application which comprises the following steps:
(I) forming a temperable flavored confectionery composition as defined above;
(II) rapidly cooling the composition of step (I) to a temperature of about 57° F. or less so that the reduced calorie fat forms a sub $\alpha$ phase;
(III) holding the cooled composition of step (II) at a temperature of about 57° F. or less for a period of time sufficient to form an effective amount of $\beta$-3 crystals from a portion of the sub $\alpha$ phase of the reduced calorie fat; and
(IV) after step (III), warming the cooled composition to a temperature in the range of from above about 57° to about 72° F. in a manner such that: (a) the remaining portion of the reduced calorie fat transforms into a stable $\beta$-3 phase; and (b) the $\beta$-3 phase formed does not melt.

Certain of the present reduced calorie fats, like cocoa butter, can be crystallized into a stable $\beta$-3 phase. However, it has ben found that the rate of crystallization of these reduced calorie fats into the $\beta$3 phase is extremely slow under standard tempering conditions used with cocoa butter-based chocolate products. This rate is sufficiently slow so as to make cocoa butter-type tempering of flavored confectionery compositions containing these reduced calorie fats commercially unattractive.

Surprisingly, it has been found that tempering according to said Ehrman et al application provides a commercially attractive process that is simpler than even the standard tempering conditions used with cocoa butter-based chocolate product. In particular, this tempering process can be carried out during the normal warehousing and distribution of the flavored confectionery product. These desirable results are achieved by taking advantage of the ability of these reduced calorie fats to transform into the desired stable $\beta$-3 phase, via the less stable sub $\alpha$ phase. This transformation of the reduced calorie fats from the sub $\alpha$ phase to the stable $\beta$-3 phase according to this tempering process occurs without undesired bloom formation. The resulting tempered products also have the desired firmness and mouthmelt of cocoa butter-based chocolate products.

The present reduced calorie fats can also be fortified with vitamins and minerals, particularly the fat-soluble vitamins. U.S. Pat. No. 4,034,083 of Mattson (incorporated by reference herein) discloses polyol fatty acid polyesters fortified with fat-soluble vitamins. The fat-soluble vitamins include vitamin A, vitamin D, vitamin E, and vitamin K. Vitamin A is a fat-soluble alcohol of the formula $C_{20}H_{29}OH$. Natural vitamin A is usually found esterified with a fatty acid; metabolically active forms of vitamin A also include the corresponding aldehyde and acid. Vitamin D is a fat-soluble vitamin well known for use in the treatment and prevention of rickets and other skeletal disorders. Vitamin D comprises sterols, and there are at least 11 sterols with vitamin D-type activity. Vitamin E (tocopherol) is a third fat-soluble vitamin which can be used in the present invention. Four different tocopherols have been identified (alpha, beta, gamma and delta), all of which are oily, yellow liquids, insoluble in water but soluble in fats and oils. Vitamin K exists in at least three forms, all belonging to the group of chemical compounds known as quinones. The naturally occurring fat-soluble vitamins are $K_1$ (phylloquinone), $K_2$ (menaquinone), and $K_3$ (menadione). The amount of the fat-soluble vitamins employed herein to fortify the present reduced calorie fat materials can vary. If desired, the reduced calorie fats can be fortified with a recommended daily allowance (RDA), or increment or multiple of an RDA, of any of the fat-soluble vitamins or combinations thereof.

Vitamins that are nonsoluble in fat can similarly be included in the present reduced calorie fats. Among these vitamins are the vitamin B complex vitamins, vitamin C, vitamin G, vitamin H, and vitamin P. The minerals include the wide variety of minerals known to be useful in the diet, such as calcium, magnesium, and zinc. Any combination of vitamins and minerals can be used in the present reduced calorie fat.

The present reduced calorie fats are particularly useful in combination with particular classes of food and beverage ingredients. For example, an extra calorie reduction benefit is achieved when the fat is used with noncaloric or reduced calorie sweeteners along or in combination with bulking agents. Noncaloric or reduced calorie sweeteners include, but are not limited to, aspartame; saccharin; alitame, thaumatin; dihydrochalcones; cyclamates; steviosides; glycyrrhizins, synthetic alkoxy aromatics, such as Dulcin and P-4000; sucrolose; suosan; miraculin; monellin; sorbitol, xylitol; talin; cyclohexylsulfamates; substituted imidazolines; synthetic sulfamic acids such as acesulfame, acesulfam-K and n-substituted sulfamic acids; oximes such as perilartine; rebaudioside-A; peptides such as aspartyl malonates and succanilic acids; dipeptides; amino acid based sweeteners such as gem-diaminoalkanes, meta-aminobenzoic acid, L-aminodicarboxylic acid alkanes, and amides of certain alpha-aminodicarboxylic acids and gem-diamines; and 3-hydroxy-4-alkyloxyphenyl aliphatic carboxylates or heterocyclic aromatic carboxylates.

The reduced calorie fats can be used in combination with other noncaloric or reduced calorie fats, such as branched chain fatty acid triglycerides, triglycerol ethers, polycarboxylic acid esters, sucrose polyethers, neopentyl alcohol esters, silicone oils/siloxanes, and dicarboxylic acid esters. Other partial fat replacements useful in combination with the reduced calorie fats are medium chain triglycerides, highly esterified polyglycerol esters, acetin fats, plant sterol esters, polyoxyethylene esters, jojoba esters, mono/diglycerides of fatty acids, and mono/diglycerides of short-chain dibasic acids.

Certain of the present reduced calorie fats are particularly useful in reduced calorie fat compositions comprising certain substantially nonabsorbalbe, substantially nondigestible polyol polyesters. See U.S. application Ser. No. 329,629 to Paul Seiden, Corey J. Kenneally, Thomas J. Wehmeier, Mary M. Fox and Raymond L. Niehoff (P&G Case 3947), filed Mar. 28, 1989, which is incorporated by reference. These reduced calorie fat compositions comprise:

a. from about 10 to about 65% of an edible, substantially nonabsorbable, substantially nondigestible polyol fatty acid polyester having at least 4 fatty acid ester groups, wherein the polyol is selected from sugars and sugar alcohols containing from 4 to 8 hydroxy groups and wherein each fatty acid group has from 2 to 24 carbon atoms; and b. from about 35 to about 90% reduced calorie triglycerides selected from MMM, MLM, MML, LLM, LML and LLL triglycerides, and mixtures thereof; wherein M is a saturated fatty acid residue selected from $C_6$ to $C_{10}$ saturated fatty acids, and mixtures thereof; wherein L is a saturated fatty acid residue selected from $C_{18}$ to $C_{24}$ saturated fatty acids, and mixtures thereof; wherein the reduced calorie triglycerides comprise: (1) at least about 85% combined MLM, MML, LLM and LML; and (2) up to about 15% combined MMM and LLL triglycerides, and wherein the fatty acid composition of the reduced calorie triglycerides comprises: (1) from about 10 to about 70% $C_6$ to $C_{10}$ saturated fatty acids; and (2) from about 30 to about 90% $C_{18}$ to $C_{24}$ saturated fatty acids.

Food products can comprise these reduced calorie fat compositions as the sole fat ingredient, or in combination with other fat ingredients such as triglyceride oils. These food products include frying oils for salted snacks and other fried foods, firm chocolate-flavored products such as chocolate-flavored candy bars or chips, as well as cooking and salad oils that are clear at room temperature, i.e., about 70° F. (21.1° C.), and preferably at lower temperatures, e.g., at about 50° F. (10° C.).

Surprisingly, certain of the present reduced calorie fats can function as anti-anal leakage agents for the polyol polyesters. In addition, the combination of the polyol polyesters with these reduced calorie fats provides significant advantages over the use of either component alone. The advantages provided by these combinations include: (1) increased caloric reduction; (2) textural/taste benefits (e.g., less waxiness/greasiness, improved mouthmelt); (3) less color degradation during frying; and (4) less high temperature volatility and foaming during frying.

Bulking or bodying agents are useful in combination with the reduced calorie tats in many food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose and microcrystalline cellulose. Other suitable bulking agents include gums (hydrocolloids), starches, dextrins, fermented whey, tofu, maltodextrins, polyols, including sugar alcohols, e.g. sorbitol and mannitol, and carbohydrates, e.g. lactose.

Similarly, food and beverage compositions can be made that combine the present reduced calorie fats with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers include fiber from whole citrus peel, citrus albedo, sugar beets, citrus pulp and vesicle solids, apples, apricots, and watermelon rinds.

These dietary fibers may be in a crude or purified form. The dietary fiber used may be of a single type (e.g. cellulose), a composite dietary fiber (e.g. citrus albedo fiber containing cellulose and pectin), or some combination of fibers (e.g. cellulose and a gum). The fibers can be processed by methods known to the art.

The reduced calorie fats can also contain minor amounts of optional flavorings, emulsifiers, anti-spattering agents, anti-sticking agents, anti-oxidants, or the like.

Of course, judgment should be exercised to make use of appropriate reduced calorie fats and combinations of these fats with other food ingredients. For example, a combination of sweetener and fat would not be used where the specific benefits of the two are not desired. The fat and fat ingredient combinations are used where appropriate, and in the proper amounts.

Many benefits are obtained from the use of the present reduced calorie fats in food and beverage compositions, either when used alone or in combination with the ingredients discussed above. A primary benefit is the calorie reduction achieved when the fat is used as a total or partial fat replacement. This calorie reduction can be increased by using combinations of the present fats with reduced calorie sweeteners, bulking agents, or other reduced calorie or noncaloric fats. Another benefit which follows from this use is a decrease in the total amount of fats in the diet. Foods or beverages made with the reduced calorie fats instead of triglyceride fats will also contain less cholesterol, and the ingestion of these foods can lead to reduced serum cholesterol and thus reduced risk of heart disease.

A related benefit is that the use of the reduced calorie fats allows the production of foods and beverages that are stable in terms of shelf stability and penetration stability. Compositions made with the reduced calorie fats have acceptable organoleptic properties, particularly taste and texture.

Dietary foods can be made with the reduced calorie fats to meet special dietary needs, for example, of persons who are obese, diabetic, or hypercholesterolemic. The reduced calorie fat can be a major part of a low-fat, low-calorie, low-cholesterol diet, and they can be used alone or in combination with drug therapy or other therapy. Combinations of food or beverage products made with the reduced calorie fat can be used as part of a total dietary management regimen, based on one or more of these products, containing the reduced calorie fat along or in combination with one or more of the above-mentioned ingredients, to provide one or more of the above-mentioned benefits.

This discussion of the reduced calorie fats uses, combinations, and benefits, is not intended to be limiting or all-inclusive. IT is contemplated that other similar uses and benefits can be found that will fall within the spirit and scope of this invention.

G. Analytical Methods

1. Carbon Number Profile (CNP)

The carbon number profile (CNP) of the triglycerides (i.e. MML/MLM, MLL/LML, MMM and LLL) can be determined by programmed temperature-gas chromatography (GC) using a short fused silica column coated with methyl silicone for analysis and characterization of the composition by molecular weight. The glycerides are separated according to their respective carbon numbers, wherein the carbon number defines the total number of carbon atoms on the combined fatty acid residues. The carbon atoms on the glycerol molecule are not counted. Glycerides with the same carbon number will elute as the same peak. For example, a triglyceride composed of three $C_{16}$ (palmitic) fatty acid residues will co-elute with triglycerides made up of one $C_{14}$ (myristic), one $C_{16}$ and one $C_{18}$ (stearic) fatty acid residue or with a triglyceride composed of two $C_{14}$ fatty acid residues and one $C_{20}$ (arachidic) fatty acid residue.

Preparation of the fat sample for analysis is as follows: The fat sample is heated at 80° C. until completely melted. A 500 microl. portion of the melted sample is pipetted into a 5 ml. volumetric flask, and is then diluted to volume using chloroform. A 250 microl. portion of the solution in the flask is transferred to an autosampler vial and then 1.0 ml. of bis (trimethylsilyltrifluoroacetamide) (BSTFA) is pipetted into the vial which is then capped. The contents in the vial are heated for 15 minutes at 70° C. and then cooled before analysis.

For determining the CNP-GC of the prepared fat samples, a Hewlett-Packard 5890 series gas chromatograph equipped with temperature programming and a hydrogen flame ionization detector is used together with a Hewlett-Packard 3351B data system. A 2 m. long, 0.25 mm. diameter fused silica capillary column coated with a thin layer of methyl silicone (J&W DB-1) is also used. A glass insert packed with silated glass wool (HP 18740-80190) and a high temperature graphite O-ring is used with this column. The column is heated in an oven where temperature can be controlled and increased according to a specified pattern by the temperature programmer. The hydrogen flame ionization detector is attached to the outlet port of the column. The signal generated by the detector is amplified by an electrometer into a working input signal for the data system and recorder. The recorder prints out the gas chromatograph curve and the data system electronically integrates the area under the curve. The following instrument conditions are used with the gas chromatograph:

| | |
|---|---|
| Septum purge | 2-3 mil./min. |
| Split ratio | 85/1-100/1 |
| Hydrogen carrier gas | 2-4 ml./min. |
| Hydrogen pressure | 40 psi |
| Detector temp. | 375° C. |
| Detector hydrogen | 30 ml./min |
| Detector air | 330 ml./min. |
| Detector make-up | 25 ml./min. |

1.0 microl. of the prepared fat sample is injected by a gas-tight syringe, or a HP 7673A microdrop injector with tray thermostated to 25° C., into the sample port of the chromatograph. The components in the sample port are warmed up to a temperature of 340° C. and swept by a hydrogen carrier gas to push the components into the column. The column temperature is initially set at 80° C. and held at this temperature for 0.5 min. The column is then heated up to a final temperature of 340° C. at a rate of 15° C./min. The column is maintained at the final temperature of 340° C. for an additional 25 minutes.

The chromatographic peaks generated are then identified and the peak areas measured. Peak identification is accomplished by comparison to known pure glycerides previously programmed into the data system. The peak area as determined by the data system is used to calculate the percentage of glycerides having a particular Carbon Number ($C_N$) according to the following equation:

$$\%C_N = (Area\ of\ C_N/S) \times 100$$

wherein S = sum of Area of $C_N$ for all peaks generated.

The Area of $C_N$ is based upon the actual response generated by the chromatograph multiplied by a response factor for glycerides of the particular Carbon Number. These response factors are determined by comparing the actual responses of a mixture of pure fatty acids and glycerides of various Carbon Numbers to the known amounts of each fatty acid or glyceride in the mixture. A fatty acid/glyceride generating an actual response greater than its actual amount has a response factor less than 1.0; likewise, a fatty acid/glyceride generating a response less than that of its actual amount has a response factor of greater than 1.0. (Typical response factors for the triglycerides of interest are 0.95 to 1.0.) A typical mixture of fatty acids and glycerides used (in a chloroform solution) is as follows:

| Component | Carbon No. | Amount (mg./ml.) |
|---|---|---|
| Octanoic | 8 | 0.5 |
| Decanoic | 10 | 0.5 |
| Palmitic acid | 16 | 0.5 |
| Monopalmitin | 16 | 0.5 |
| Behenic acid | 22 | 0.5 |
| Monostearin | 18 | 0.5 |
| Dipalmitin | 32 | 0.5 |
| Palmitostearin | 34 | 0.5 |
| Distearin | 36 | 0.5 |
| Tripalmitin | 48 | 1.5 |
| Dipalmitostearin | 50 | 1.5 |
| Distearopalmitin | 52 | 1.5 |
| Tristearin | 54 | 1.5 |
| Tribehenin | 66 | 1.5 |

2. Fatty Acid/Fatty Acid Anhydride Reaction Mixtures a. Reagents and equipment

Gas chromatograph: HP 5890 with capillary split injection

Autosampler: HP 767A microdrop injector with tray thermostated to 25° C.

Column: J&W DB-1, 2 meters, ×0.25 mm., 0.25 microm. film thickness

Carrier gas: hydrogen

BSTFA (N,O)-Bis (Trimethylsilyltrifluoroaceamide)

Chloroform

Internal standard: tricaprin b. Instrument conditions (flow settings)

Septum purge: 4 ml./min.

Hydrogen gas flow rate: 4 ml./min.

Hydrogen pressure: 40 psi

Split ratio: 85/1 c. Sample preparation

Heat sample at 80° C. until completely melted.

Pipette a 500 microl. portion of melted sample into a 5 ml. volumetric flask and dilute to volume using chloroform. Transfer 250 microl. portion of solution in flask to autosampler vial, add 1.0 ml. of fresh BSFTA, cap vial, and heat to 70° C. for 15 minutes. Cool sampler vial before analysis.

d. Oven conditions

Oven temperature (initial value): 40° C.

Oven temperature (initial time): 0.5 min.

Progress rate: 15° C./min.

Oven temperature (final value): 350° C.

Oven temperature (final time): 10 min.

Detection temperature: 375° C.

Injection temperature: 340° C.

e. Calibration/Results

Analytical results are expressed as a wt. % of total fatty acids/fatty acid anhydrides in the samples. Reagent standards for $C_8$, $C_{10}$ and $C_{12}$ fatty acids and fatty acid anhydrides are used for calibration and for determination of response factors. Typical fatty acid response factors are 1.05, while those for the fatty acid anhydrides are 0.8-0.85, relative to the tricaprin internal standard.

3. Thin Layer Chromatography (TLC)

a. Reagents and Materials

Phosphomolybdic Acid (Aldrich 22, 185-6 99%)

Petroleum Ether (reagent grade)

Ethyl Ether (reagent grade)

Glacial Acetic Acid (reagent grade)

Methanol (reagent grade)

Chloroform (reagent grade)

HPTLC-GHLF 57527 Analtech TLC Plates (High Performance Thin-Layer Chromatography Plates)

Hard-layer silica coating/absorbents that fluoresce b. Procedure

Dissolve 5 drops of reaction mixture in 1 ml $CHCl_3$. Use micropipet to spot 1-2 ml of solution on plate, 1.5 cm from base of plate. Wait for spot to dry and develop plate in suitable TLC chamber. Use filter paper in TLC chamber to increase solvent vapor phase. Remove plate from chamber and dry thoroughly in fume hood with an air stream. Quickly dip dried plate into 5% phosphomolybdic acid in methanol solution, making sure area of interest is submerged. Place TLC plate on hot plate st at a temperature where spots develop in 30 seconds to 1 minute. When all spots have developed, remove from hot plate and, for long term storage, either photocopy or photograph TLC plates within 2-4 hours of plate development as the developed areas will fade over time. From the origin the order of component elution is monoglyceride/glycerine, 1,2- and 2,3-diglycerides, fatty acids, triglycerides (usually single spot if high MML/MLM purity), and unsaponifiable materials, e.g., soaps, etc.

c. Notes on Procedures

Plate development takes 6-8 minutes.

Plate must be dry before phosphomolybdic acid treatment or streaking will occur.

Keep solvent level in chamber below spot origin on plates.

Allow solvent front to develop to 1 cm from top of plate.

Keep TLC chamber closed or solvent system composition will change.

Mark origin and final solvent front point to calculate Rf values.

Phosphomolybdic acid solution should be prepared fresh once a month.

Development solution should be made fresh every week.

To help identify spots, run standards of known compounds to establish Rf values of the following compounds: monoglyceride standard: monobehenin fatty acid standard: capric or caprylic acid or behenic acid diglyceride standard: ML or MM diglyceride triglyceride standard: any medium or long chain saturated
fatty acid triglyceride (prefer MML/MLM)

The procedure has a sensitivity of less than 0.4 wt.% relative to diglycerides spiked into the triglyceride/fatty acid matrix.

5. Free Fatty Acid Titration (as Oleic)

a. Reagents
1. Ethyl alcohol—3A. Titrated to the phenolphthalein endpoint with 0.1N sodium hydroxide solution.
2. Sodium hydroxide—0.1N or 0.25N.
3. Phenolphthalein—0.5% in alcohol.

b. Apparatus
1. Balance—torsion.
2. Magnetic stirrer. Labline Magnestir, or equivalent.
3. Stirring bars. Magnetic, 0.25 in O.D.×1.5 in. length, Teflon-covered.
4. Buret. Digital—25 ml., Fisher Cat. #03-840. Adapter set to fit solution bottle—Fisher Cat. #13-688-106.
5. pH meter. Beckman Expandomatic IV pH meter.
6. Electrode. Combination—Orion Cat. #910400/Fisher Cat. #14-641-681.

c. Reference Standard

A reference standard lauric acid (4.5 g.) dissolved in white mineral oil (1335 g.), is run with each group of samples. The results are compared with the known value for the reference standard to determine the accuracy of the sample results.

d. Titration

1. Weigh approximately 50 g. of sample into a 250 ml. Erlenmeyer flask to the nearest 0.01 g. Weigh a 15 g. sample of the lauric acid reference standard.
2. Add 50 ml. of hot neutralized 3A alcohol to the melted sample in the flask. Note: Sample should be heated only long enough to liquefy before the titration. Overheating increases the possibility of hydrolysis occurring and a consequent elevation of the free fatty acid content.
3. Add about 0.5 ml. of phenolphthalein indicator to the sample.
4. Titrate the sample with the 0.1N NaOH solution. For light-colored samples, titrate while stirring until a very pale pink color is evident in the stirring emulsion. For dark samples, titrate until the alcohol layer, when allowed to separate, is pale pink (color should persist for at least 30 seconds). Occasionally the free fatty acid content of an apparently fresh sample is quite high. If 50 g. of sample titrates over 10 ml. with 0.1N NaOH, titrate it with 0.25N NaOH. For very high free fatty acid-glyceride mixtures, it may be necessary to weigh 10 g. of sample and titrate with 0.25n NaOH.
5. Record the titration volute (T).

e. Calculation $$\% \text{ free fatty acid (as oleic)} = \frac{T \times N \times 28.2}{\text{Sample Weight (g.)}}$$

Where:
T = sample titration in ml. of NaOH
N = normality of NaOH
28.2 = milliequivalent weight of oleic acid × 100

H. Specific Illustrations of MML/MLM Triglyceride-Making According to the Process of the Present Invention The following are specific illustrations of the process for making MML/MLM triglycerides according to the process of the present invention:

EXAMPLE 1

High purity (98.2% pure) monostearin was reacted with reagent grade (99% pure) capric ($C_{10:0}$) and caprylic ($C_{8:0}$) fatty acid anhydrides as follows:

Approximately 2.25 grams of monostearin was placed into a 25 ml. three-neck round bottom flask and melted at 120° C. with reagent grate (99% pure) capric (Sigma C-3652) and caprylic (Sigma C-3517) fatty acid anhydrides. The weight ratio of $C_{10:0}$ to $C_{8:0}$ anhydrides was 55:45, while the mole ratio of fatty acid anhydrides to monostearin was 2.2:1. The mixture was heated with a thermostatically controlled heating mantel and was vigorously stirred with a magnetic stirrer. Gaseous nitrogen was bubbled through the esterification mixture at the rate of 0.8 l/min. by using a gas dispersion tube and flow meter. Progress of the esterification was monitored by thin-layer chromatography (TLC) using high performance silica plates and a 75% petroleum ether/25% diethyl ether/1% acetic acid development solvent, followed by charring with 5% phosphomolybdic acid in anhydrous methanol on a hot plate. The esterification was carried out for a period of 4.25 hours at 120° C. and was stopped after the elimination of all diglycerides (i.e., measured level less than 0.4%). Analysis of the esterified product obtained indicated a 0.2% MMM, 99.4% MML/MLM, and 0.4% MLL/LML triglyceride composition. (As determined by CNP (acid/anhydride free basis), "MMM" = $C_{24}$ to $C_{30}$, "MML/MLM" = $C_{32}$ to $C_{40}$, and "MLL/LML" = $C_{42}$ to $C_{48}$.)

EXAMPLE 2

High purity (98.1% pure) monobehenin was esterified at 160° C. with a mixture of reagent grade (99% pure) $C_{8:0}$ and $C_{10:0}$ fatty acid anhydrides (45:55 weight ratio) to determine the effect of mole ratio of anhydrides to monobehenin on MML/MLM triglyceride purity. The general esterification and monitoring procedures were similar to those described in Example 1. Each esterification was stopped upon conversion of all diglycerides (i.e. measured level of less than 0.4%) into triglyceride products. The results of the various esterification runs are shown below:

| Anhydride to Monobehenin Mole Ratio | Glyceride Composition of Product* | | |
|---|---|---|---|
| | MMM (%) | MML/MLM (%) | MLL/LML (%) |
| 2.2:1 | 1.8 | 96.1 | 2.2 |
| 4.4:1 | 2.2 | 96.2 | 1.6 |
| 8.1:1 | 1.8 | 97.6 | 0.6 |

*By CNP (acid/anhydride free basis). "MMM" = $C_{24}$ to $C_{34}$. "MML/MLM" = $C_{36}$ to $C_{44}$. and "MLL/LML" = $C_{46}$ to $C_{56}$

EXAMPLE 3

Monobehenin having various levels of impurities such as glycerol and dilong ($C_{22:0}$) diglycerides was esterified with a mixture of capric ($C_{10:0}$) and caprylic ($C_{8:0}$) fatty acid anhydrides using general esterification and monitoring procedures similar to those described in Example 1. The monobehenin used in these esterifications was prepared by either ethanol fractional crystallization or by molecular distillation of a crude behenic acid/glycerol reaction product. The esterification runs were carried out using a mixture of reagent grade (99% pure) $C_{10:0}$ and $C_{8:0}$ fatty acid anhydrides (55:45 weight ratio) at an anhydride to monobehenin mole ratio of 2.2:1 and at reaction temperature of 120° C. or 160° C. The results of the esterification runs involving various levels of glycerol (Gly) or diglyceride (DiGly) in the monobehenin starting (Mono) material are shown below:

| Monobehenin Purity | | | Esterification | Glyceride Composition of Product* | | |
|---|---|---|---|---|---|---|
| Mono (%) | Gly (%) | DiGly (%) | Temp. (°C.) | MMM (%) | MML/ MLM (%) | MLL/ LML (%) |
| 98.1 | 0.1 | 0.5 | 160 | 1.5 | 96.6 | 1.9 |
| 76.6 | 7.9 | 7.0 | 160 | 15.0 | 77.7 | 7.3 |
| 86.6 | — | 12.6 | 160 | 0.1 | 88.6 | 11.3 |
| 98.1 | 0.1 | 0.5 | 120 | 2.0 | 96.2 | 1.9 |
| 95.8 | 0.4 | 2.6 | 120 | 6.3 | 92.7 | 0.9 |

*By CNP, as in Example 2

EXAMPLE 4

Monobehenin was esterified with various mixtures of $C_{8:0}/C_{10:0}$ fatty acid anhydrides to determine the effect of impurities in the anhydride starting materials on MML/MLM triglyceride purity. In these esterification runs, reagent grade (99% pure) capric (Sigma C-3642) and caprylic (Sigma C-3517) fatty acid anhydrides were spiked with either acetic acid (Fisher A38-212) or acetic anhydride (Mallinkrodt 2420). The monobehenin was commercially produced by molecular distillation of a behenic acid/glycerol reaction product feed. Each of the esterification runs was carried out using a 2.2:1 fatty acid anhydride to monobehenin mole ratio at 160° C. for two hours. The fatty acid anhydrides were added on an equal mole basis (55% $C_{10:0}$/45% $C_{8:0}$ weight ratio). The monobehenin starting material contained 98.1% monoglyceride, 0.1% glycerol, 0.5% diglyceride, 0.3% diglycerol, and 0.5% behenic acid. In the spiked runs, acetic acid or acetic anhydride was added (on a $C_{10:0}/C_{8:0}$ anhydride basis) at a 1% or 1.5% level, respectively. The general esterification and monitoring procedures were similar to those described in Example 1. The results of these esterification runs are shown below:

| Anhydride Purity | Glyceride Composition of Product* | | |
|---|---|---|---|
| | MMM (%) | MML/MLM (%) | MLL/LML (%) |
| Control | 1.5 | 96.6 | 1.9 |
| 1% acetic acid | 2.6 | 95.2 | 2.2 |
| 1.5% acetic anhydride | 2.4 | 95.3 | 2.3 |

*By CNP, as in Example 2.

EXAMPLE 5

Monobehenin (98.1% purity) was esterified with capric ($_{10:0}$) and caprylic ($C_{8:0}$) fatty acid anhydrides (99% purity) by various addition methods to determine the effect of sequential esterification on MML/MLM triglyceride purity. In this evaluation, an esterification temperature of either 120° C. or 160° C. was used. The anhydrides were added at a total weight ratio of 55% $C_{10:0}$/45% $C_{8:0}$, with a total mole ratio of fatty acid anhydride to monobehenin of 2.2:1. In the sequential addition runs, $C_{8:0}$ anhydride was initially added at varying levels up to the stoichiometric mole ratio that would theoretically convert the monobehenin to the respective diglyceride. After addition of all of the $C_{8:0}$ anhydride, a 20% mole excess of $C_{10:0}$ anhydride was then added to complete the esterification. The control esterification runs involved the addition of a 10% mole excess of both $C_{8:0}$ and $C_{10:0}$ anhydride initially to the monobehenin starting material. The esterifications runs were carried out and monitored by procedures similar to those described in Example 1 and were stopped after conversion of all of the diglycerides (i.e. measured level of less than 0.4%). The results of these esterification runs are shown below:

| Anhydride Addition Method | Esterification | | Glyceride Composition of Product* | | |
|---|---|---|---|---|---|
| | Temp. (°C.) | Time (Hr.) | MMM (%) | MMM/MLM (%) | MLL/LML (%) |
| Control (2.2 moles $C_{8:0}$/ $C_{10:0}$ added) | 160 | 1.0 | 1.5 | 96.6 | 1.9 |
| Sequential (0.5, 0.4, and 0.1 moles $C_{8:0}$ added, then 1.2 moles $C_{10:0}$ added) | 160 | 4.5 | 3.5 | 87.4 | 9.1 |
| Sequential (0.9 and 0.1 moles $C_{8:0}$ added, then 1.2 moles $C_{10:0}$ added) | 160 | 4.5 | 3.1 | 89.8 | 7.1 |
| Control (2.2 moles $C_{8:0}$/ $C_{10:0}$ added) | 120 | 3.0 | 2.0 | 96.2 | 1.9 |
| Sequential (0.5 and 0.5 moles $C_{8:0}$ added, then 1.2 moles $C_{10:0}$ added) | 120 | 22.0 | 4.4 | 91.1 | 4.5 |

*By CNP, as in Example 2.

EXAMPLE 6

Three runs were carried out where monobehenin was esterified with mixtures of $C_{8:0}$ and $C_{10:0}$ fatty acid anhydrides (45:55 eight ratio) to determine the effect of mixed, asymmetrical ($C_{2:0}C_{8:0}$ or $C_{2:0}/C_{10:0}$) anhydrides, and their conversion to symmetrical anhydrides, on MML/MLM triglyceride purity. In the first esterification run (Control), monobehenin was esterified with high purity $C_{8:0}C_{10:0}$ fatty acid anhydrides from which residual asymmetrical anhydride impurities had been completely removed. In the control run, a stoichiometric amount of acetic anhydride (Mallinkrodt 2420) was reacted with capric (Aldrich 15, 376-1) and caprylic (Aldrich 15, 375-3) fatty acids at 165°-185° C. for two hours in a 250 ml. three-necked round bottom flask equipped with a thermostatically controlled heating manual, stir bar, and a 10-inch Vigreux distillation column. Heat was applied slowly to distill the evolved acetic acid. Upon completion of the reaction, 67.3% fatty acids/unknowns, 13.5% asymmetrical anhydrides, and 29.1% symmetrical anhydrides were measured by GC in the reaction mixture. This fatty acid/anhydride mixture was purified of the asymmetrical anhydrides by heating at 197°-232° C. for 45 minutes while applying an increasing vacuum of from 760 mm Hg to 200 mm Hg. followed by an additional vacuum of from 200 mm Hg to 17 mm Hg. Upon completion of the distillation of the residual acetic acid and acetic anhydride, the asymmetrical anhydrides were completely converted to symmetrical anhydrides, i.e. GC analysis indicated 13.5% fatty acids/unknowns and 86.5% symmetrical anhydrides in the mixture. This purified/converted fatty acid/anhydride mixture was added at a 4.4:1 mole ratio to high purity (98.1% pure) monobehenin in a heated, stirred nitrogen blanketed round-bottom flask. The esterification reaction was carried out for 40 minutes at 160° C., until all diglycerides had been converted (i.e. measured level of less than 0.4%). Analysis of the esterified product indicated a 1.5% MMM, 97.3% MML/MLM and 1.3% MLL/LML triglyceride composition. (As determined by CNP (acid/anhydride free basis), "MMM"=$C_{24}$ t $C_{34}$, "MML/MLM"=$C_{36}$ to $C_{44}$, and "MLL/LML"=$C_{46}$ to $C_{56}$.)

In the second esterification run, a stoichiometric amount of acetic anhydride (Mallinkrodt 2420) was reacted with capric (P&G C1095) and caprylic (P&G C895) fatty acids under total reflux at 157° C. for 1 hour. The reactor used was similar to the control run except that a 120° C. reflux condenser replaced the distillation column. GC analysis indicated that the resulting reaction mixture contained 64.5% fatty acids/unknowns, 18% asymmetrical anhydrides, and 17.4% symmetrical anhydrides. The fatty acid/anhydride reaction mixture was purified by heating at 205°-210° C. under reduced pressure (255 mm Hg) for 45 minutes. GC analysis of this purified fatty acid/anhydride mixture indicated 47.5% symmetrical anhydrides, 3.9% asymmetrical anhydrides, and 48.5% fatty acids/unknowns. This purified fatty acid/anhydride mixture was added at a 5:1 mole ratio to high purity (98.1% pure) monobehenin and esterified for 30 minutes at 160° C. under a nitrogen blanket until all diglycerides had been converted (i.e. measure level of less than 0.4%). CNP analysis of the resulting esterified product indicated a 15.2% MMM/SML, 83.1% MML/MLM, and 1.7% MLL/LML triglyceride composition. (The designation "SML" refers to triglycerides containing acetic, medium and long chain fatty acid residues.)

In the third esterification run, acetic anhydride (Mallinkrodt 2420), caprylic acid (P&G C895), capric acid (P&G C1095), and high purity (98.1% pure) monobehenin at a 1:1:1:0.2 mole ratio, were reacted at a temperature of 160° C. (This mole ratio theoretically converts all the fatty acids to the anhydride form for subsequent esterification of monobehenin at a 5:1 mole ratio.) The reactor used was identical to that of the first two runs with a 120° C. reflux condenser and a nitrogen sparge for removal of evolved acetic acid. After 1 hour, the reaction temperature was increased to 210° C. for conversion of asymmetrical anhydrides to symmetrical anhydrides, and to complete the esterification of monobehenin. After an additional hour under these reaction conditions, the mixture was cooled to ambient temperature. CNP analysis of the resulting product indicated a 15.0% SSL, 47.2% SML, 36.5% MML/MLM, and 1.3% MLL/LML triglyceride composition. (The "SSL" designation refers to triglycerides containing two acetic acid fatty acid residues and one long chain fatty acid residue, while the "SML" designation refers to triglycerides containing acetic, medium and long chain fatty acid residues.)

EXAMPLE 7

Fatty acid anhydrides were prepared by acetic anhydride dehydration of capric ($C_{10:0}$) and caprylic ($C_{8:0}$) fatty acids in a 3-liter, three-necked reaction flask equipped with magnetic stir bar, heating mantel, nitrogen sparge, thermowatch, and temperature controlled reflux condensor. Two reaction batches were made using a 1:1:1 mole ratio of acetic anhydride (Eastman PM 6355), capric fatty acid (Henkel C8-98/100), and caprylic fatty acid (Henkel C10-98/100). The combined reagents were reacted at 136°-160° C. for 1 hour under reflux using a 70°-100° C. condensor. Nitrogen stripping at the rate of 0.2 l/min. was applied as the reaction temperature was progressively increased to 225° C. over a α hour time period to distill residual acetic acid, acetic anhydride, and to convert asymmetrical anhydrides to the symmetrical anhydrides. GC analysis of the combined batches indicated 27% fatty acids/unknowns and 73% $C_{8:0}/C_{10:0}$ symmetrical anhydrides. Overall yield of fatty acid anhydride was 64% for the combined batches. Two esterification runs were carried out in a 3-liter round-bottom flask by esterifying high purity (98.1% pure) monobehenin with the combined fatty acid/anhydride mixtures at a 2.1:1 anhydride to monobehenin mole ratio and esterification temperatures of 120° C. and 160° C., respectively. The monobehenin was added to the fatty acid/anhydride mixture, heated to the respective esterification temperature, and then sparged with nitrogen at the rate of 0.3 l/min. The esterification progress was monitored by TLC as described in Example 1. The triglyceride composition of the two esterified products obtained is shown below:

| Esterification | | Glyceride Composition of Product* | | |
|---|---|---|---|---|
| Temp. (°C.) | Time (Hr.) | MMM (%) | MML/MLM (%) | MLL/LML (%) |
| 120 | 6.0 | 2.4 | 96.3 | 1.3 |
| 160 | 1.25 | 2.2 | 95.9 | 2.0 |

*By CNP, as in Example 2.

The two esterified products were combined and then stripped of residual fatty acids and anhydrides using a 2-inch diameter Pope wiped-film glass evaporator. The combined product was preheated to 70° C. and then fed into the evaporator which operated at a pressure of 0.025-0.250 mm Hg, a temperature of 180°-200° C., a 228 rpm wiper speed, and a 15°-20° C. internal condensor temperature. Flow rate was adjusted to minimize MML/MLM triglyceride removal. A 51% cut rate was obtained with a 94.5% yield of stripped product having a 1.9% MMM, 96.5% MML/MLM, and 1.6% MLL/LML triglyceride composition, as measured by CNP. The residual fatty acid level was 0.3% (as oleic acid).

The stripped mixture was then bleached at 78° C. for 3.5 hours with 5% Filtrol ® F-105 bleaching earth/1% Norit ® 2203 activated carbon under nitrogen sparging. As measured by CNP, the bleached product had a 2.2% MMM, 96.5% MML/MLM and 1.3% MLL/LML triglyceride composition. The bleached product was then deodorized at a temperature of 232° C., a pressure of 3 mm Hg, and a 0.096 ml/min. g. steam sparge rate for 2 hours. Composite CNP analysis indicated that the deodorized product had a 1.9% MMM, 95.8% MML/MLM, and a 2.2% MLL/LML triglyceride composition. The resulting deodorized product was bland, taste-free and suitable for use in a variety of confectionery applications as a cocoa butter substitute.

What is claimed is:

1. A process for selectively making MML/MLM triglycerides, wherein M is a $C_6$–$C_{10}$ fatty acid residue or mixture thereof and L is a $C_{18}$–$C_{24}$ fatty acid residue or mixture thereof, said process comprising the step of esterifying an at least about 60% pure $C_{18}$–$C_{24}$ fatty acid monoglyceride or mixture thereof with an at least about 50% pure $C_6$–$C_{10}$ fatty acid anhydride or mixture thereof at a temperature of from about 90° to about 190° C. in the absence of an esterification catalyst, wherein the mole ratio of fatty acid anhydride to monoglyceride is at least about 2:1.

2. The process of claim 1 wherein the monoglyceride is at least about 90% pure $C_{18}$–$C_{24}$ saturated fatty acid monoglyceride or mixture thereof, and wherein the fatty acid anhydride is at least 50% pure $C_6$–$C_{10}$ saturated fatty acid anhydride or mixture thereof.

3. The process of claim 2 wherein said esterification step is carried out in a solvent-free anhydrous system.

4. The process of claim 3 wherein the monoglyceride is at least about 95% pure, with about 3% or less LL diglycerides, about 1% or less glycerol, and about 1% or less glycerol dehydration products.

5. The process of claim 4 wherein the monoglyceride is at least about 98% pure, with about 1% or less LL diglycerides, about 0.5% or less glycerol, and about 0.5% or less glycerol dehydration products.

6. The process of claim 4 wherein the source of fatty acid anhydride comprises up to about 50% $C_6$–$C_{10}$ saturated fatty acid or mixture thereof.

7. The process of claim 6 wherein the source of fatty acid anhydride is at least about 70% pure in $C_6$–$C_{10}$ saturated fatty acid anhydride or mixture thereof, with up to about 30% $C_6$–$C_{10}$ saturated fatty acid or mixture thereof, and about 0.5% or less combined acetic acid, acetic anhydride, and asymmetrical fatty acid anhydrides.

8. The process of claim 7 wherein the mole ratio of fatty acid anhydride to monoglyceride is from about 2:1 to about 5:1.

9. The process of claim 8 wherein the mole ratio of fatty acid anhydride to monoglyceride is from about 2:1 to about 3:1.

10. The process of claim 3 wherein said esterification step is carried out at a temperature of from about 120° to about 160° C.

11. The process of claim 10 wherein said esterification step is carried out for from about 0.5 to about 6 hours.

12. The process of claim 11 wherein said esterification step is carried out for from about 1 to about 3 hours.

13. The process of claim 12 wherein the level of MML/MLM triglycerides is at least about 85% and wherein the level of diglycerides is about 1% or less after said esterification step.

14. The process of claim 13 which comprises the further steps of bleaching the MML/MLM triglycerides, followed by deodorizing the bleached MML/MLM triglycerides.

15. The process of claim 13 comprising the further step of purifying the MML/MLM triglycerides obtained after said esterification step to decrease the level of combined fatty acids/anhydrides to about 0.5% or less, the level of MMM triglycerides to about 3% or less and the level of MLL/LML triglycerides to about 3% or less.

16. The process of claim 15 wherein said purification step includes a molecular distillation step to separate the fatty acids/anhydrides and MMM triglycerides as the distillate fraction from the MML/MLM and MLL/LML triglycerides.

17. The process of claim 16 wherein said purification step includes a second molecular distillation step to separate the MML/MLM triglycerides as the distillate fraction from the MLL/LML triglycerides.

18. The process of claim 3 wherein the fatty acid anhydride is melted prior to said esterification step and wherein the monoglyceride is slowly added to the melted anhydride at a controlled rate of addition during said esterification step such that the level of unreacted monoglyceride is about 0.2% or less.

19. A solvent-free anhydrous process for selectively making MML/MLM triglycerides, wherein M is a $C_8$ saturated fatty acid residue, a $C_{10}$ saturated fatty acid residue, or mixture thereof, and L is at least about 90% behenic fatty acid residues, said process comprising the step of esterifying an at least about 90% pure monobehenin monoglyceride, with an at least about 70% pure $C_8$ saturated fatty acid anhydride, $C_{10}$ saturated fatty acid anhydride, or mixture thereof, at a temperature of from about 120° to about 160° C. for from about 0.5 to about 6 hours in the absence of an esterification catalyst, wherein the mole ratio of the fatty acid anhydride to monoglyceride is from about 2:1 to about 5:1.

20. The process of claim 19 wherein the source of fatty acid anhydride is at least about 70% pure $C_8$ saturated fatty acid anhydride.

21. The process of claim 19 wherein the source of fatty acid anhydride is at least bout 70% pure $C_{10}$ saturated fatty acid anhydride.

22. The process of claim 19 wherein the weight ratio of $C_8$ to $C_{10}$ saturated fatty acid anhydrides is from about 30:70 to about 45:55.

23. The process of claim 22 wherein the source of the fatty acid anhydride comprises up to about 30% of a mixture of $C_8$ and $C_{10}$ saturated fatty acids, and about 0.5% or less combined acetic acid, acetic anhydride, and asymmetrical fatty acid anhydrides.

24. The process of claim 23 wherein the monobehenin monoglyceride is at least about 95% pure, with about 3% or less LL diglycerides, about 1% or less glycerol and about 1% or less glycerol dehydration products.

25. The process of claim 24 wherein the monobehenin monoglyceride is at least about 98% pure, with about 1% or less LL diglycerides, about 0.5% or less glycerol and about 0.5% or less glycerol dehydration products.

26. The process of claim 19 wherein said esterification step is carried out for from about 1 to about 3 hours.

27. The process of claim 26 wherein the level of MML/MLM triglycerides is from about 88 to about 98% and wherein the level of diglycerides is about 1% or less after said esterification step.

28. The process of claim 27 which comprises the further steps of bleaching the MML/MLM triglycerides, followed by deodorizing the bleached MML/MLM triglycerides.

29. The process of claim 27 comprising the further step of purifying the MML/MLM triglycerides obtained after said esterification step to decrease the level of combined fatty acids/anhydrides to about 0.5% or less, the level of MMM triglycerides to about 3% or less and the level of MLL/LML triglycerides to about 3% or less.

30. The process of claim 29 wherein said purification step includes a molecular distillation step to separate the fatty acids/anhydrides and MMM triglycerides as the distillate fraction from the MML/MLM and MLL/LML triglycerides.

31. The process of claim 30 wherein said purification step includes a second molecular distillation step to separate the MML/MLM triglycerides as the distillate fraction from the MLL/LML triglycerides.

32. The process of claim 19 wherein the fatty acid anhydride is melted prior to said esterification step and wherein the monobehenin monoglyceride is slowly added to the melted anhydride at a controlled rate of addition such that the level of unreacted monoglyceride is about 0.2% or less.

33. The process of claim 3 wherein the monoglyceride is at least about 90% pure $C_{20}$–$C_{24}$ saturated fatty acid monoglyceride or mixture thereof.

* * * * *